(12) United States Patent
Storer et al.

(10) Patent No.: US 12,296,542 B2
(45) Date of Patent: May 13, 2025

(54) METHOD OF WELDING A SLEEVE TO A TUBE, AND DEVICE OBTAINED THEREBY

(71) Applicant: ENKI S.R.L., Concesio (IT)

(72) Inventors: Matteo Storer, Collebeato (IT); Nicola Spatarella, Brescia (IT); Simona Pasotti, Concesio (IT); Monica Venturini, Bovezzo (IT)

(73) Assignee: ENKI S.R.L., Concesio (IT)

( * ) Notice: Subject to any disclaimer, the term of this patent is extended or adjusted under 35 U.S.C. 154(b) by 230 days.

(21) Appl. No.: 18/075,568

(22) Filed: Dec. 6, 2022

(65) Prior Publication Data
US 2023/0173767 A1 Jun. 8, 2023

(30) Foreign Application Priority Data
Dec. 6, 2021 (EP) ..................................... 21425078

(51) Int. Cl.
*B29C 61/02* (2006.01)
*B29C 65/00* (2006.01)
(Continued)

(52) U.S. Cl.
CPC ...... *B29C 66/73715* (2013.01); *B29C 61/025* (2013.01); *B29C 66/5221* (2013.01);
(Continued)

(58) Field of Classification Search
CPC .......... A61M 25/0045; A61M 25/1025; A61M 25/1034; B29C 61/003; B29C 61/006; B29C 61/02; B29C 61/025; B29C 65/10; B29C 65/14; B29C 65/1403; B29C 65/1406; B29C 65/1409; B29C 65/1412;
(Continued)

(56) References Cited

U.S. PATENT DOCUMENTS 4,938,676 A * 7/1990 Jackowski .......... B29C 49/6445
425/530
5,423,755 A 6/1995 Kesten et al.
(Continued)

FOREIGN PATENT DOCUMENTS

EP 0873759 B1 6/2005

OTHER PUBLICATIONS

European Search Report, application No. EP 21 42 5078, completed Jun. 3, 2022, 9 pages.

*Primary Examiner* — Michael A Tolin
(74) *Attorney, Agent, or Firm* — WARE FRESSOLA MAGUIRE & BARBER LLP

(57) ABSTRACT

A method of welding a sleeve (10) to a tube (20) includes putting onto end portions (11) of the sleeve (10) respective protective elements (40), of a material that cannot be fused with the materials of the sleeve (10) and of the outer coating (24) of the tube (20); applying on each end portion (11) of the sleeve (10) covered by a protective element (40) a respective heat-shrink element (30); supplying each heat-shrink element (30) with a quantity of heat (Q) which by heating it causes it to shrink and compress the respective end portion (11) of the sleeve (10) against the tube (20), where this quantity of heat (Q) is transmitted to the end portion (11) of the sleeve (10) to obtain a welding of the sleeve (10) to the tube (20) and produce a device (1) comprising the tube (20) with the sleeve (10).

7 Claims, 2 Drawing Sheets

(51) Int. Cl.
*B29K 75/00* (2006.01)
*B29L 9/00* (2006.01)
*B29L 23/00* (2006.01)

(52) U.S. Cl.
CPC ....... *B29K 2075/00* (2013.01); *B29L 2009/00* (2013.01); *B29L 2023/22* (2013.01)

(58) Field of Classification Search
CPC ......... B29C 65/16; B29C 65/18; B29C 65/68; B29C 66/004; B29C 66/0042; B29C 66/0044; B29C 66/005; B29C 66/032; B29C 66/0324; B29C 66/0326; B29C 66/1122; B29C 66/5221; B29C 66/53241; B29C 66/71; B29C 66/723; B29C 66/73116; B29C 66/73715; B29C 66/73921; B29C 66/8122; B29L 2031/7542; B29L 2031/7543
See application file for complete search history.

(56) References Cited

U.S. PATENT DOCUMENTS

| | | | |
|---|---|---|---|
| 6,139,525 | A | 10/2000 | Davis-Lemessy et al. |
| 8,440,090 | B2 * | 5/2013 | Haslinger ......... A61M 25/0054 |
| | | | 604/523 |
| 2002/0115963 | A1 * | 8/2002 | Clarke ................ B29C 66/1122 |
| | | | 604/103 |
| 2003/0135231 | A1 | 7/2003 | Goodin et al. |
| 2006/0182907 | A1 | 8/2006 | Atanasoska et al. |
| 2007/0255207 | A1 * | 11/2007 | Hangai ............. A61M 25/1036 |
| | | | 604/96.01 |
| 2008/0077173 | A1 | 3/2008 | Flanagan |
| 2012/0245517 | A1 | 9/2012 | Tegels |
| 2022/0126401 | A1 * | 4/2022 | Pischlar ............. B29C 65/1619 |

* cited by examiner

METHOD OF WELDING A SLEEVE TO A TUBE, AND DEVICE OBTAINED THEREBY

TECHNICAL FIELD

The present invention is part of the sector of biomedical tubes manufacturing, and in particular it relates to a method of welding a sleeve to a tube, conduit, catheter and the like.

PRIOR ART

A method of welding a sleeve to a tube is known, with the single or multi-lumen tube made of relatively flexible but inextensible material, is for example polymeric material such as polyamide, polyether block amide, polycarbonate, or the like, and with the sleeve of consistently elastic material, for example polymeric material such as polyolefins or polyurethane, assigned to be inflated to make a balloon. The materials of the sleeve and the tube do not allow mutual fusion.

This known method essentially involves the steps of:
- donning the sleeve on the tube at an opening that sets in fluid connection the outside of the tube with the inside of one or more of its lumens;
- mechanically fastening the sleeve to the tube by gluing or tying the ends of the sleeve to the external surface of the tube.

The main disadvantage of the known method consists in the fact that the mechanical constraint by gluing or tying the sleeve to the pipe does not guarantee the tightness of the constraint itself in correspondence with stresses of particular extent.

Another disadvantage of the known method consists in the fact that the mechanical constraint involves a thickening and a discontinuity in the overall diameter of the ends of the sleeve.

A method of welding a sleeve to a tube is also known, with the tube and the sleeve made of materials suitable for mutual welding by fusion.

This latter known method essentially involves the steps of:
- donning the sleeve on the tube at the opening;
- welding the ends of the sleeve to the external surface of the tube providing enough heat to the ends of the sleeve to weld them to the external surface of the tube by fusion of the respective materials.

In the common use of the tube with inflatable sleeve obtained by means of this known method, it is usually necessary that the tube has an almost constant cross-section as the pressure and the curvature vary, is made of a sufficiently flexible but inextensible material, and that the sleeve is made of a suitably elastic material so that it can be inflated; a disadvantage of this method lies in the fact that, requiring the use of mutually weldable materials, it restricts the choice to materials which may be unsuitable for making the tube or the sleeve.

Document US 2006/182907 A1 discloses a medical device formed at least in part from a microfibrillar polymer-polymer composite, the microfibrillar polymer-polymer composite comprising a polymer matrix and oriented polymer microfibrils, and a method of making the same.

DISCLOSURE OF THE INVENTION

The main object of the present invention is to propose a method of welding a sleeve to a tube by fusing the sleeve to the tube, where the sleeve and the tube are made of respective materials that do not allow mutual fusion and welding, for example polymeric materials such as polyolefins and/or polyurethane for the sleeve and polyamide and/or polyether block amide and/or polycarbonate for the tube.

Another object is to propose a method of welding a sleeve to a tube in which the mechanical and pneumatic tightness of the sleeve on the pipe is extremely effective.

BRIEF DESCRIPTION OF THE DRAWINGS

The features of the invention are highlighted hereafter with specific reference to the accompanying schematic and non-scale drawings in which.

DETAILED DESCRIPTION

Figure 1:
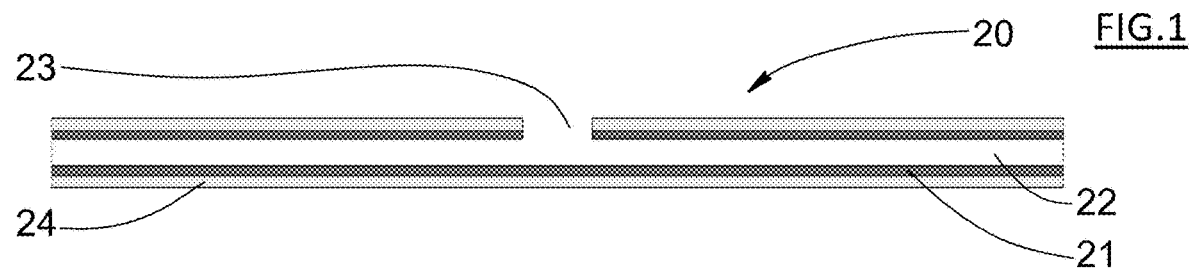
FIGS. 1-5, 7 and 8 illustrate a sequence of steps of the method of welding a sleeve to a tube object of the present invention.
Figure 2:
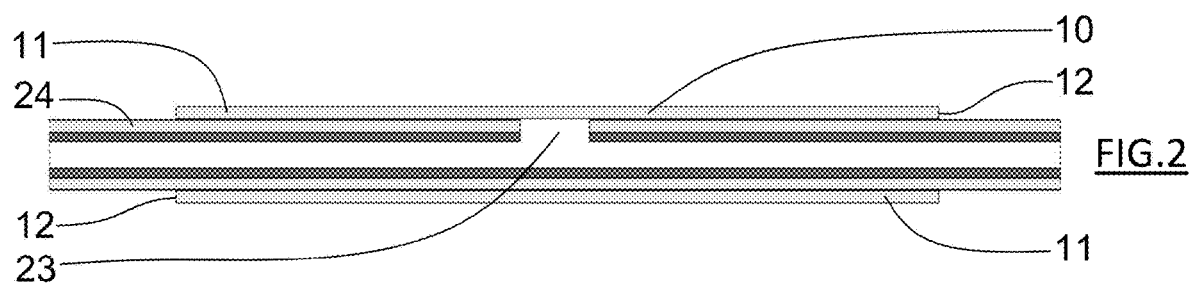
Figure 3:
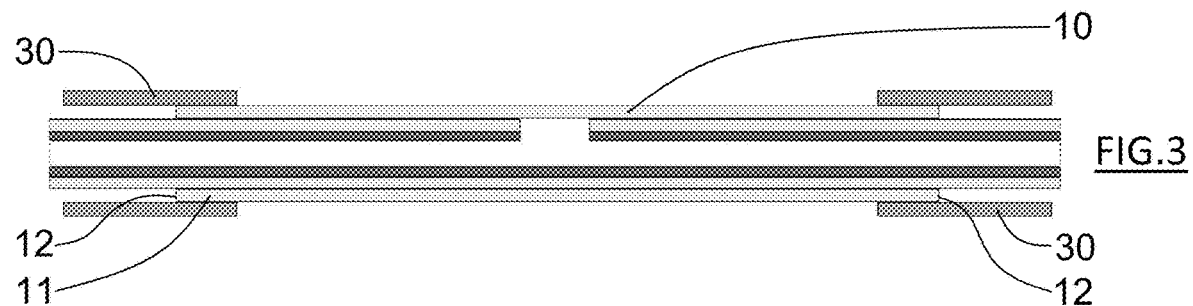
Figure 4:
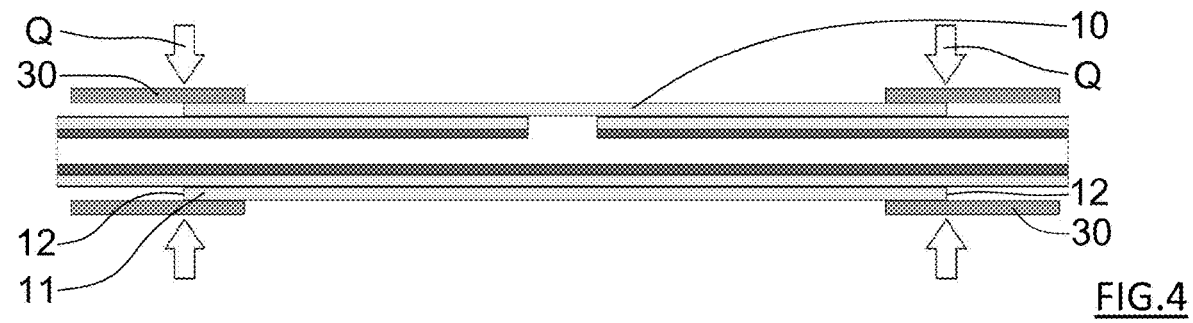
Figure 5:
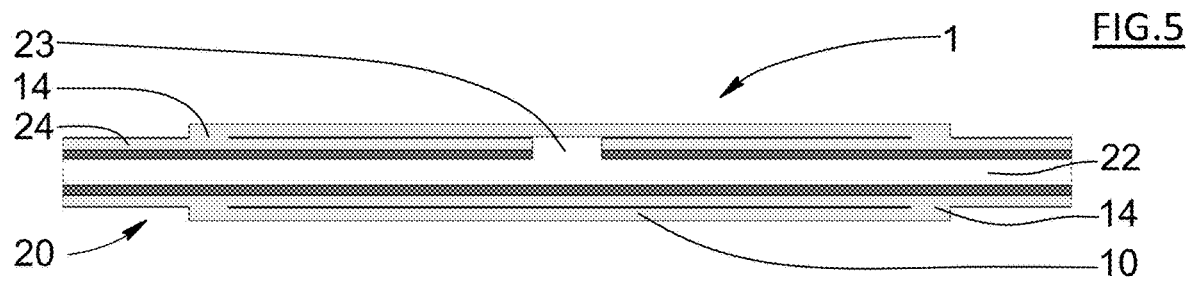
Figure 6:
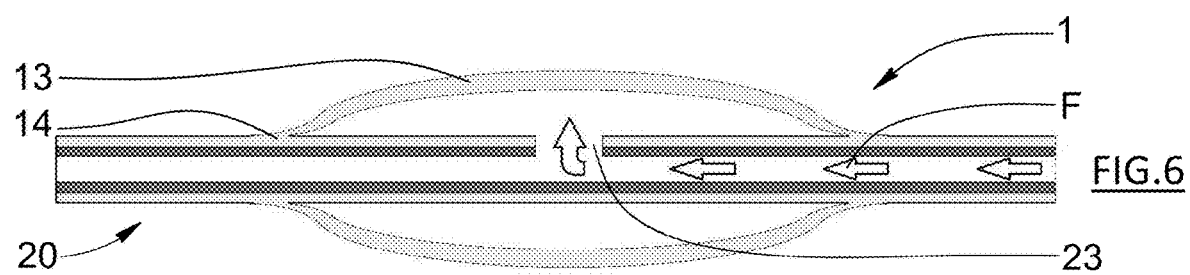
FIG. 6 illustrates a view of the device object of the present invention in correspondence with a use condition thereof.

With reference to FIGS. 1-8, the present invention relates to a method of welding a sleeve 10 to a tube 20, to obtain a device 1 of FIGS. 5 and 6 assigned to be used, for example, in the medical field as a catheter with inflatable balloon, in the hydraulic field as a probe, in any application where a tube or probe with an inflatable balloon is useful.

The tube 20 has at least one outer layer 21, of a first material, which encloses a longitudinal lumen 22, set in fluid communication with the outside of the tube 20 also through lateral openings 23, preferably one, of slot or eyelet type. Optionally, the tube 20 can have one or more inner layers and/or more lumens, where at least one of the lumens 22 is in fluid communication with the outside of the tube 20 through said lateral opening or openings 23.

The tube 20 can flex adequately in correspondence with a use condition U, for example during its insertion and use inside the body of a patient, bending but without throttling. The cross section of the tube 20 remains practically constant as the pressure inside the tube 20 and the curvature of the tube 20 vary.

The sleeve 10 has tubular shape, with two end portions 11 opposite and open at respective ends 12. The length of the sleeve 10 is greater than the longitudinal dimension of the lateral opening 23 of the tube 20 to which the ends 12 of the sleeve 10 must be welded.

The sleeve 10 is mainly made of an elastic second material, suitable for inflation but not suitable for welding or fixing by fusion with the first material of the outer layer 21 of the tube 20.

The method includes the steps of:
- coating at least a tract, including the lateral opening 23, of the outer layer 21 of the tube 20 with an outer coating 24 of a third material compatible with fusion with the second material of the sleeve 10, leaving the lateral opening 23 uncovered;
- putting the sleeve 10, the internal diameter of which must be similar to or slightly greater than the external diameter of the coated tube 20, onto said coated tract of the tube 20 at the lateral opening 23, so that the lateral opening 23 of the tube 20 is located between the two end portions 11 of the sleeve 10, which are in contact with the outer coating 24 of the tube 20;
- putting onto respective thin protective elements 40 on the portions of the sleeve 10 and possibly of the tube 20 assigned for these heat-shrink elements 30, made of a non-stick and/or non-fusible material with the materials of the heat-shrink element 30, of the sleeve 10 and of the outer coating 24 of the tube 20;

applying on at least one part of each end portion 11 of the sleeve 10 covered by a protective element (40) a respective heat-shrink element 30, of tubular, annular or planar wound shape;

supplying each heat-shrink element 30 with a quantity of heat Q which, by heating it, causes it to shrink and compress the respective end portion 11 of the sleeve 10 against the outer coating 24 of the tube 20, where concurrently this quantity of heat Q is transmitted to the end portion 11 of the sleeve 10 and of the outer coating 24 of the tube 20 bringing them to a temperature of mutual welding, for example equal to or higher than the melting temperature of the sleeve 10 and of the outer coating 24, obtaining the device 1 comprising the tube 20 with the sleeve 10 so welded.

Preferably but not necessarily, the method provides to remove the heat-shrink elements 30 from the device 1, and/or to remove the protective elements 40 from the device 1.

In correspondence with the use condition U, the device 1 can be inserted into the body of a patient from the side of an insertion end of the tube 20 itself; by pressure forcing a fluid F into the lumen 22 of the tube 20 in communication with the opening 23 from its opposite open end, the elastic sleeve 10 is assigned to inflate forming a balloon 13, while the tube 20, rigid to transverse deformation, does not change its own dimension.

The outer surface of the outer layer 21 of the tube 20 can be coated with the third material for example by extrusion, or by spraying, or by means of other processes commonly known to the skilled in the art, to make the outer coating 24.

All the steps of the method can be indifferently carried out manually by an operator or automatically by a machine.

In the preferred embodiment, a polymeric material is for example used for the first material of the outer layer 21 of the tube 20, comprising at least one of polyamide (PA), polyether block amide (PEBA), polycarbonate (PC) and/or the like; the second material of the sleeve 10 is for example chosen polymeric, comprising at least one of polyolefins, polyurethane (PU) and/or the like; a polymeric material, for example, is used for the third material of the outer coating 24 of the tube 20, comprising at least one of polyolefins, polyurethane (PU) and/or the like.

In the exemplified case, the second material and the third material are mutually weldable by fusion, but they are not suitable for welding with the first material by fusion, as is commonly known to the expert in the field.

Preferably, the method provides in particular to completely coat the outer layer 21 of the tube 20 with the outer coating 24 of the third material.

The friction and/or interference between the external surface of the tube 20 and its outer coating 24 are generally sufficient in themselves to mutually anchor and seal the tube 20 and the external coating 24.

The heat-shrink elements 30, in an initial condition in correspondence with the step of applying them 30 onto the sleeve 10, have an internal diameter equal to or slightly greater than the external diameter of the sleeve 10 fitted on the tube 20.

The protective element 40 is for example a tubular or planar shaped sheath, such that it can be fitted on or wrapped around the respective end portion 11 of the sleeve 10 interposing between this and the respective heat-shrink element 30, and with a thin thickness, such as not to significantly alter the distribution of the heat Q from the heat-shrink element 30 to the sleeve 10 and to the tube 20 thereunder. Each protective element 40 covers at least a part of the respective end portion 11 of the sleeve 10 and an adjacent portion of the tube 20 not covered by the sleeve 10.

The material of the protective element 40 is preferably polyamide or similar material, which cannot be welded by fusion with the materials of the heat-shrink element 30, of the sleeve 10 and of the outer coating 24 of the tube 20. The length of the protective element 40 can be equal, smaller or even greater than that of the respective heat-shrink element 30, provided that, once the protective element 40 has been put on, it separates the heat-shrink element 30 from the sleeve 10 and from the tube 20 at least at the end 12 of the sleeve 10 and at the parts of the sleeve 10 and of the outer coating 24 assigned to be fused by the externally supplied heat Q.

The function of the protective element 40 is essentially to prevent the heat-shrink element 30 from welding to the tube 20 or to the sleeve 10 in correspondence with the supply step of the heat Q.

In correspondence with the step of supplying the heat Q to weld the sleeve 10 to the tube 20, each heat-shrink element 30 distributes this heat Q on its own internal surface, and therefore, through its respective protective element 40, to the respective underlying end portion 11 of the sleeve 10, protecting the latter from local temperature surges which could cause an irreparable degradation in its structural and/or chemical composition.

The temperature of the part of the end portion 11 of the sleeve 10 affected by the flow of the heat Q increases at least up to the melting temperature of the second material of the sleeve 10; the further propagation of the heat Q through the thickness of the sleeve 10 also leads to the possible partial melting of the third material of the outer coating 24 of the tube 20 directly in contact with the molten part of the sleeve 10; concurrently, the distribution of the heat Q along the heat-shrink element 30 causes a longitudinal and diametral shrinking of the latter, which presses on the end portion 11 of the sleeve 10, now melted; thanks also to this compression action, therefore, the two molten materials interpenetrate and mix with each other, at least partially, in a welding region 14, leading to the mutual welding of the sleeve 10 and the tube 20.

After the welding of the two molten materials, the heat Q initially supplied to the heat-shrink element 30 spreads further from the welding region 14 to its neighborhood, causing a lowering of the temperature in the welding region 14 itself below the melting temperature.

Once the end portions 11 of the sleeve 10 and the adjacent tracts of the outer coating 24 of the tube 20 have cooled and are once again in the solid state, it is possible to carry out the step of removing the heat-shrink elements 30 from the device 1. This removal can take place in various alternative ways, for example by pulling the heat-shrink elements 30 off the tube 20 from both its ends, or by longitudinally cutting the heat-shrinking elements 30 to sever their lateral surface and thus release them from the tube 20, or by similarly breaking their lateral surface by pulling a tab or sturdy wire, not shown, associated inside the heat-shrink elements 30 prior to their application on the sleeve 10.

The protective elements 40 can be removed from the device 1 in various ways similar to those provided for the removal of the heat-shrink elements 30.

The removal of the protective elements 40 preferably takes place after the step of removing the heat-shrink elements 30, but alternatively it can also be carried out before this step, especially if the protective element 40 is longer than the respective heat-shrink element 30 and therefore protrudes outside of the latter, making it suitable for being grabbed and removed from under the heat-shrink element 30.

The protective elements 40 are indispensable especially if the heat-shrink elements 30 are made of polymeric material compatible with fusion with the materials of the sleeve 10 and/or of the outer coating 24 of the tube 20, such as for example materials containing polyolefin and/or polyurethane. Without interposing the protective elements 40, in fact, the melting temperature of the heat-shrink elements 30 similar to that of the sleeve 10 and of the tube 20 would also lead to the welding of the heat-shrink elements 30 with the sleeve 10 and the tube 20 in correspondence with the step of supplying the heat Q, then making it impossible to accurately carry out the step of removing the heat-shrink elements 30 from the device 1.

Once the heat-shrink elements 30 have been removed, it is optionally possible to finish the welding regions 14 of the sleeve 10 to the tube 20, for example by chamfering or tapering the ends 12 of the sleeve 10 by filing, turning or cutting, especially if these have not been affected by the melting and therefore protrude clearly from the surface profile of the coated tube 20: this could indeed cause discomfort or injuries to the patient in correspondence with the use condition U of the device 1.

The heat Q is preferably supplied to the heat-shrink elements 30 by conduction through contact with heating means and/or by convection through a flow of hot gas and/or by electromagnetic radiation.

The heating means are for example resistive elements.

The electromagnetic radiation originates, for example, from incandescent or halogen lamps, which radiate energy in the visible and/or infrared and/or ultraviolet spectra; alternatively and preferably laser sources are used so that the irradiation is more intense, in which case the energy namely the heat Q is supplied to the heat-shrink elements 30 in quantities that are well-defined and located with extreme precision. In particular, the use of a pulsed laser allows to concentrate a considerable amount of energy into pulses of reduced duration and extension; this energy propagates through the relatively thin heat-shrink elements 30 to the underlying sleeve 10 and tube 20, causing the latter to melt and the heat-shrink elements 30 to shrink; however, the short duration of the pulse leaves no way for the heat Q to diffuse appreciably in the longitudinal direction, allowing the portions of tube 20 and sleeve 10 affected by fusion to be well localized.

Figure 7:
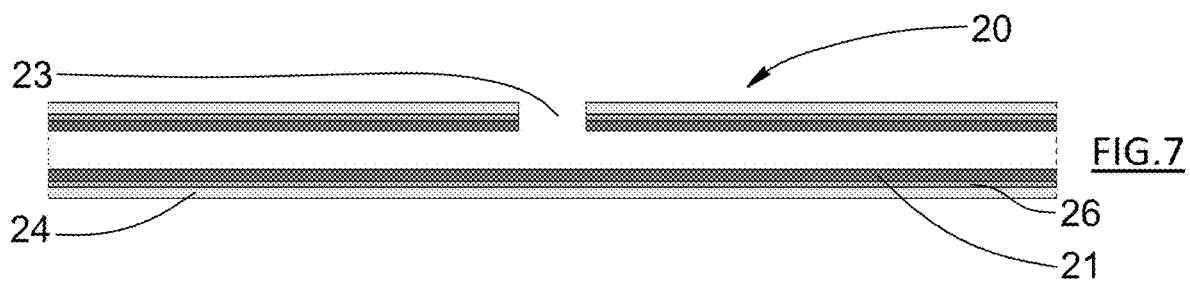
Figure 8:
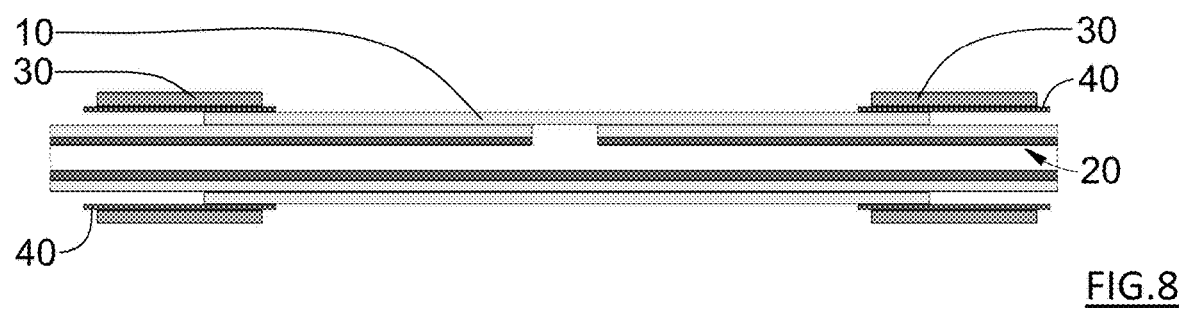

Referring now to FIG. 7, in order for the outer coating 24 to adhere more tightly to the outer layer 21, before the coating step, a variant of the method optionally provides for applying on the tube 20 an intermediate layer 26 of a binding material to chemically bond the outer layer 21 and the outer coating 24 of the tube 20 and/or making them adhere to each other. After the coating step, this intermediate layer 26 is interposed between the outer layer 21 and the outer coating 24 of the tube 20.

The binding material acts as a primer or adhesive between the second material and the third material, being able to chemically and/or mechanically bind to both and thus making them adhere to each other, and is for example a glue (epoxy, acrylic, cyanoacrylate, polyurethane, silicone, and/or similar) or preferably low density polyethylene (LDPE).

In another variant thereof, the method provides for arranging each heat-shrink element 30 in such a way that it covers, in addition to at least one already mentioned part of the respective end portion 11 of the sleeve 10, also the respective end 12 of the sleeve 10 and at least an adjacent portion of the outer coating 24 of the tube 20 not covered by the sleeve 10, for example each heat-shrink element 30 being approximately centered on the respective end 12 of the sleeve 10. This arrangement is particularly convenient, because by supplying the heat Q to each heat-shrink element 30 almost at the respective end 12 of the sleeve 10 such heat Q propagates both to the end portion 11 of the sleeve 10 and to the underlying outer coating 24 of the tube 20 and directly to the outer coating 24 adjacent to the sleeve 10 but not covered by this. Therefore, part of the end portion 11 of the sleeve 10, part of the outer coating 24 of the tube 20, and in particular the end 12 of the sleeve 10 are involved in the fusion. The concurrent compressing action exerted by the heat-shrink element 30 thus also involves the discontinuity at the end 12 of the sleeve 10, and following the mutual fusion between the sleeve 10 and the outer coating 24 of the tube 20 and the subsequent solidification, the end portions 11 of the sleeve 10 are welded in a single body to the tube 20 in respective welding regions 14, which are tapered or rounded.

In order for the heat-shrink elements 30 not to be melted and not to be welded in turn with the sleeve 10 or with the outer coating 24 of the tube 20, they are preferably made of a material not suitable for fusion with the materials of the sleeve 10 and of the outer coating 24. Said material, for example, is a polymeric material that shrinks upon heating, but with a higher melting temperature than that of the materials to be melted; for this reason the preferred choice is polytetrafluoroethylene (PTFE), or for example polyethylene (PE), polyvinyl chloride (PVC), neoprene, and/or similar.

The present invention also relates to a device 1 made according to the method described above. Referring also to FIGS. 5 and 6, this device 1 comprises:

a tube 20 having at least one outer layer 21 of a first material and at least one lumen 22 in fluid communication with the outside of the tube 20 through at least one lateral opening 23;

a sleeve 10 having two end portions 11 opposite and open at respective ends 12 and made of a second material not suitable for fusion with the first material of the outer layer 21 of the tube 20.

The tube 20 is externally coated, at least for a tract in correspondence with the lateral opening 23, preferably for its entire length, with an outer coating 24 of a third material compatible with fusion with the second material.

The sleeve 10, assigned to be inflated to make a balloon 13 in correspondence with a use condition U of the device 1, is put on the coated tube 20 at the lateral opening 23 and has its end portions 11 welded by fusion to the outer coating 24 of the tube 20 at respective welding regions 14 of the device 1.

Optionally, the material of the sleeve 10, at the ends 12 of the latter, is welded in a single body with the outer coating 24 of the tube 20; in this way the ends 12 of the sleeve 10 protrude from the coated tube 20 but are solidly fixed thereto.

In a variant of the device 1, the ends 12 of the sleeve 10, free or welded to the tube 20, are jointed to the outer coating 24 of the tube 20 by means of a taper, i.e. the diameter of the cross section of the sleeve 10 varies continuously and monotonically at its ends 12, so that the longitudinal trend of the diameter of the device 1 shows no discontinuities at the welding regions 14.

The invention claimed is:

1. A method of welding a sleeve to a tube, the method comprising:
   providing a tube, the tube comprising an outer layer comprising a first material, the outer layer further comprising at least one lateral opening and at least one lumen in fluid communication with the outside of the tube through the at least one lateral opening;
   providing a sleeve, the sleeve comprising two end portions opposite and open at respective ends, the sleeve being made of a second material not suitable for fusion with the first material of the outer layer of the tube;
   covering at least a tract of the tube including the at least one lateral opening of the outer layer with an outer coating of a third material compatible with fusion with the second material of the sleeve;
   putting the sleeve onto said coated tract of the tube at the at least one lateral opening;
   putting respective protective elements onto the end portions of the sleeve to cover each end portion of the sleeve, the protective elements comprising a material that cannot be fused with the second material of the sleeve and the third material of the outer coating of the tube;
   applying a respective heat-shrink element on at least one part of each end portion of the sleeve covered by the respective protective element;
   supplying each heat-shrink element with a quantity of heat to cause it to shrink and compress the respective end portion of the sleeve against the tube, where this quantity of heat is transmitted to the end portion of the sleeve to bring it to a temperature equal to or higher than a melting temperature of the second material and the third material, thereby obtaining a welding of the sleeve to the tube and producing a device comprising the tube with the sleeve.

2. The method according to claim 1, comprising arranging each heat-shrink element to cover, in addition to the at least one part of the respective end portion of the sleeve, also respective ends of the sleeve and at least respective adjacent portions of the outer coating of the tube not covered by the sleeve.

3. The method according to claim 1, wherein:
   the first material comprises at least one polymeric material selected from a group consisting of polyamide, polyether block amide and polycarbonate,
   the third material comprises at least one polymeric material selected from the group consisting of polyolefins and polyurethane, and the second material comprises at least one polymeric material selected from the group consisting of polyolefins and polyurethane.

4. The method according to claim 1, further comprising:
   applying, before said covering, an intermediate layer of a binding material to bind the outer layer of the tube and the outer coating so as to mutually adhere.

5. The method according to claim 1, comprising applying the heat to the heat-shrink elements by conduction through contact with heating means, by convection, or by radiation.

6. The method according to claim 1, wherein the heat-shrink elements comprise a material that cannot be fused with the second material of the sleeve and the third material of the outer coating.

7. The method according to claim 1, wherein covering with an outer coating comprises completely coating the outer layer of the tube with the outer coating.

* * * * *